(12) United States Patent
Gardner et al.

(10) Patent No.: US 8,792,613 B2
(45) Date of Patent: Jul. 29, 2014

(54) TEST OBJECT FOR THE VALIDATION OF TRACKING IN THE PRESENCE OF MOTION

(75) Inventors: Edward Gardner, San Jose, CA (US); Thilaka Sumanaweera, Los Altos, CA (US)

(73) Assignee: CyberHeart, Inc., Mountain View, CA (US)

( * ) Notice: Subject to any disclaimer, the term of this patent is extended or adjusted under 35 U.S.C. 154(b) by 1196 days.

(21) Appl. No.: 12/621,777

(22) Filed: Nov. 19, 2009

(65) Prior Publication Data

US 2010/0137709 A1 Jun. 3, 2010

Related U.S. Application Data (60) Provisional application No. 61/116,988, filed on Nov. 21, 2008.

(51) Int. Cl.
*A61N 5/10* (2006.01)

(52) U.S. Cl.
USPC .......................................................... 378/65

(58) Field of Classification Search
USPC ........... 378/8, 65, 69; 600/411, 413, 414–416
See application file for complete search history.

(56) References Cited

U.S. PATENT DOCUMENTS

| | | | |
|---|---|---|---|
| 5,764,723 A * | 6/1998 | Weinberger et al. ............. | 378/65 |
| 6,144,875 A * | 11/2000 | Schweikard et al. ......... | 600/427 |
| 6,246,898 B1 | 6/2001 | Vesely et al. | |
| 6,501,981 B1 * | 12/2002 | Schweikard et al. ......... | 600/427 |
| 6,697,451 B2 | 2/2004 | Acharya et al. | |
| 7,151,253 B2 | 12/2006 | Varchena et al. | |
| 2003/0125622 A1 * | 7/2003 | Schweikard et al. ......... | 600/437 |
| 2003/0206614 A1 * | 11/2003 | Kendrick et al. ............. | 378/205 |
| 2004/0030235 A1 * | 2/2004 | Sasaki et al. ................... | 600/413 |
| 2004/0267113 A1 * | 12/2004 | Thomson ....................... | 600/427 |
| 2005/0180544 A1 * | 8/2005 | Sauer et al. .................... | 378/195 |
| 2006/0074292 A1 | 4/2006 | Thomson et al. | |
| 2006/0074299 A1 * | 4/2006 | Sayeh ............................ | 600/426 |
| 2006/0241403 A1 * | 10/2006 | Bruder ........................... | 600/425 |
| 2007/0244386 A1 | 10/2007 | Steckner et al. | |
| 2008/0177279 A1 | 7/2008 | Sumanaweera et al. | |
| 2008/0177280 A1 * | 7/2008 | Adler et al. .................... | 606/130 |
| 2009/0010390 A1 * | 1/2009 | Saoudi et al. .................. | 378/97 |
| 2009/0161827 A1 * | 6/2009 | Gertner et al. ................. | 378/65 |

OTHER PUBLICATIONS

Wong et al., "Quantitative Measurement of CyberKnife Robotic Arm Steering," *Technology in Cancer Research and Treatment*, Dec. 2007; 6(6):589-594, (2007); retrieved from the Internet: <<http://www.tcrt.org/OpenAccess/Wo_TCRT_6_6_589.pdf>>.
International Search Report and Written Opinion of PCT Application No. PCT/US2009/062395, mailed Dec. 29, 2009, 8 pages total.

* cited by examiner

*Primary Examiner* — Irakli Kiknadze
(74) *Attorney, Agent, or Firm* — Kilpatrick Townsend and Stockton LLP (57) ABSTRACT

A target motion simulator system for use in verifying target tracking with a radiation therapy device. The system comprises a radiation detection target coupled to a first motion actuator simulating a first motion of a first tissue and a fiducial coupled to a second motion actuator simulating a second motion of a second tissue offset from the first tissue, a component of the first motion being asynchronous with the second motion. A synthetic physiological signal generator is synchronized with the component of the first motion, wherein an output signal from the generator, in combination with a sensed position of the fiducial, may be used by the radiation therapy device in tracking the target.

30 Claims, 6 Drawing Sheets

TEST OBJECT FOR THE VALIDATION OF TRACKING IN THE PRESENCE OF MOTION

CROSS-REFERENCES TO RELATED APPLICATIONS

The present application claims the benefit under 35 USC 119(e) of U.S. Provisional Application No. 61/116,988 filed Nov. 21, 2008; the full disclosure of which is incorporated herein by reference in its entirety.

BACKGROUND OF THE INVENTION

The present invention is generally related to medical devices, systems, and methods. In particular, the present invention is in the field of quality assurance and verification for radiosurgery or radiation therapy planning.

Radiosurgery and radiotherapy are hampered by motion of the patient during dose delivery. This motion results in less dose delivered to the target structure and, potentially, more dose delivered to critical structures than desired. Patients can be immobilized to reduce inadvertent motion but breathing, cardiac motion, and bowel motions are involuntary and cannot be prevented during the treatment period. A radiosurgery system has been developed (Accuray CyberKnife with Synchrony) that can detect breathing motion of the patient and move the radiation source to compensate for this motion. This system does not compensate for cardiac or other involuntary movements. Treatment plans can be created that take into account the reduction in precision produced by patient motion in order to predict the dose delivered to moving targets or critical structures.

Test objects have been developed that simulate movements due to respiration. Wong et al. [K H Wong, S Dieterich, J Tang, K Cleary, *Quantitative Measurement of CyberKnife Robotic Arm Steering*, Technology in Cancer Research and Treatment, 6:589-594, (2007)] describe using motion tables to simulate respiratory motion of a lung tumor and skin motion simultaneously for testing of the Accuray CyberKnife system. The Wong system allows a radiation detector to be moved in three dimensions to accurately reflect the position of a lung tumor while light emitting diodes are moved to reflect the position of the skin on the chest.

Accuray and Computerized Imaging Reference Systems, Inc (CIRS) jointly developed a simpler test object for testing Accuray's CyberKnife with Synchrony system. This test object consists of two motors. One motor provides inferior-superior motion of a radiation detector and vertical motion of LED's (chest motion). A second motor rotates the radiation detector in an arc to provide additional motion.

Both the Wong and the Accuray/CIRS test objects are designed to use a fiducial in the radiation detector that can be used for alignment with the radiation delivery system. This fiducial is automatically detected by an x-ray imaging subsystem. The radiation source is then moved based on the position of the fiducial.

Neither the Wong or the Accuray/CIRS test objects has been applied to the motion of the heart. The contractile motion of the heart is substantially faster than the respiratory motion that these test objects were designed to mimic. It is speculated that the contractile motion of the heart is too fast for the Accuray CyberKnife Synchrony system to track. The Wong and CIRS/Accuray test objects are used to test the motion that is tracked and not to test the compensation applied in the treatment planning stage for motion that is not compensated.

The heart exhibits complicated motion due to contraction. This motion causes different parts of the heart to move in significantly different ways. Therefore, tracking fiducials that are not located on the target area can subject the treatment to some error. This may, however be acceptable if the treatment area is not conducive to the placement of fiducial markers. The differential motion between the fiducial location and the treated location can be compensated in the treatment plan. However, the test objects developed by Wong and CIRS/Accuray do not have any provision for differential motion between the fiducial and the radiation detector.

In light of the above, it would be desirable to develop a target motion simulator system having both respiratory and cardiac motion for use in verifying target tracking with a radiosurgery or radiation therapy device. It would be particularly beneficial if the systems were compatible with existing radiosurgery or radiation therapy systems.

BRIEF SUMMARY OF THE INVENTION

The present invention generally provides target motion simulator devices, systems, and methods for quality assurance and verification for radiosurgery or radiation therapy systems. The invention is particularly well suited for simulating motion of moving targets, such as target tissues of the heart and tissue structures adjacent the heart, that move with the respiratory and cardiac or heartbeat motion.

In a first aspect, the invention provides a target motion simulator system for use in verifying target tracking with a radiation therapy device. The system comprises a radiation detection target coupled to a first motion actuator simulating a first motion of a first tissue and a fiducial coupled to a second motion actuator simulating a second motion of a second tissue offset from the first tissue, a component of the first motion having different frequency content than the second motion. A synthetic physiological signal generator is synchronized with the component of the first motion, wherein an output signal from the generator, in combination with a sensed position of the fiducial, may be used by the radiation therapy device in tracking the target.

In another aspect, the invention provides a target motion simulator system for use in verifying target tracking with a radiation therapy device. The system comprises a radiation detection target coupled to a first motion actuator simulating both a first respiratory motion and a first cardiac motion of a first tissue and a fiducial coupled to a second motion actuator simulating a second respiratory motion of a second tissue offset from the first tissue. An electrocardiogram (EKG) output signal generator is synchronized with the first cardiac motion, wherein an EKG output signal from the EKG signal generator, in combination with a sensed fiducial position signal, may be used by the radiation therapy device in tracking the target.

Optionally, the target motion simulator system may further comprise an internal fiducial coupled to a third motion actuator simulating both the first respiratory motion and a second cardiac motion. The internal fiducial may comprise a deformable heart shell around the target or proximate the target, or a portion of a catheter. In addition, the target motion simulator system may further comprise a radiation-sensitive collateral tissue structure model coupled to a fourth motion actuator simulating both the first respiratory motion and a third cardiac motion.

In another aspect, the invention provides a target motion simulator system for simulating motion of a target having both respiratory and cardiac motion for use in verifying target tracking with a radiation therapy device. The system comprises an internal chest simulator coupled to a first respiratory motion actuator simulating internal chest respiratory motion with a radiation detection target coupled to the internal chest simulator with a first cardiac motion actuator simulating a first cardiac motion. The target movement includes both internal chest respiratory motion and first cardiac motion. An external skin simulator is coupled to a second respiratory motion actuator simulating external skin respiratory motion with an external fiducial coupled to the external skin simulator. An electrocardiogram (EKG) output signal generator synchronized with the first cardiac motion, wherein an EKG output signal from the EKG signal generator may be used by the radiation therapy device in tracking the target.

In another aspect, the invention comprises a method of using a target motion simulator system having both respiratory and cardiac motion for use in verifying target tracking with a radiation therapy device. The method comprises moving a radiation detection target with both a first respiratory motion and a first cardiac motion and moving a fiducial with a second respiratory motion. An electrocardiogram (EKG) output signal is simulated and synchronized with the first cardiac motion. The radiation detection target is tracked with the radiation therapy device using input from the EKG output signal and the external fiducial movement and fires a radiation dose from the radiation therapy device at the target.

Optionally, the method of using a target motion simulator further comprises moving an internal fiducial with the first respiratory motion and a second cardiac motion and tracking the internal fiducial with the radiation therapy device, wherein the radiation therapy device uses input from the internal fiducial movement in tracking the radiation detection target.

Optionally, the method of using a target motion simulator further comprises moving a model of a radiation-sensitive collateral tissue structure with both the first respiratory motion and a third cardiac motion, tracking the radiation-sensitive collateral tissue structure with the radiation therapy device and determining radiation received by radiation-sensitive collateral tissue structure.

In another aspect, the invention comprises a method of using a target motion simulator system having both respiratory and cardiac motion for use in verifying target tracking with a radiation therapy device. The method comprises moving an internal chest simulator simulating an internal chest respiratory motion, moving a radiation detection target coupled to the internal chest simulator simulating a first cardiac motion, and moving an external fiducial coupled to an external skin simulator simulating external skin respiratory motion. Simulating an electrocardiogram (EKG) output signal synchronized with the first cardiac motion and tracking the radiation detection target and external fiducial with the radiation therapy device using input from the EKG output signal and the external fiducial movement, and firing a radiation from the radiation therapy device at the target.

Optionally, the method of using a target motion simulator further comprises determining radiation received by the target.

Optionally, the method of using a target motion simulator further comprises moving an internal fiducial coupled to the internal chest simulator simulating a second cardiac motion and tracking the internal fiducial with the radiation therapy device, wherein the radiation therapy device uses input from the internal fiducial movement in tracking the radiation detection target.

Optionally, the method of using a target motion simulator further comprises moving a radiation-sensitive collateral tissue structure coupled to the internal chest simulator simulating a third cardiac motion, tracking the radiation-sensitive collateral tissue structure with the radiation therapy device and determining radiation received by the radiation-sensitive collateral tissue structure.

In another aspect, the invention provides a simulator system for simulating motion of a target for use in verifying target tracking with a radiation therapy device. The system comprises a movable primary actuator stage with a radiation detection target coupled to the primary actuator stage with a first movable secondary actuator stage, a combination of movement from the primary actuator stage and first secondary actuator stage simulating both a first respiratory motion and a first cardiac motion. A fiducial is coupled to the primary actuator stage with a second movable secondary actuator stage, a combination of movement from the primary actuator stage and second secondary actuator stage simulating a second respiratory motion, and an electrocardiogram (EKG) output signal synchronized with the first cardiac motion, wherein the EKG output signal may be used by the radiation therapy device in tracking the target.

DETAILED DESCRIPTION OF THE INVENTION

The present invention generally provides target motion simulator devices, systems, and methods for quality assurance and verification for radiosurgery or radiation therapy systems. The invention is particularly well suited for simulating motion of moving targets, such as target tissues of the heart and tissue structures adjacent the heart, that move with the respiratory and cardiac or heartbeat motion. The cardiac motion is typically considerably faster than the respiration motion and the invention uses simulations of both motions in the target motion. The target motion simulator may be correlated to a heart signal sensor such as an electrocardiogram (ECG) or (EKG), with the EKG output signal being used by the radiation therapy device in tracking the target. Multiple models may be employed, including separation of the target motion into a cardiac motion and a respiration motion. In other embodiments, the target motion may be correlated to both cardiac and respiratory motion. Internal and external fiducials may be used, with each fiducial being moved with either respiratory motion, cardiac motion, or both. A radiation-sensitive collateral tissue structure or critical structure may also be simulated having respiratory motion, cardiac motion, or both.

The present invention may take advantage of many components included in or derived from known radiation delivery system components. Suitable system components may comprise:

1. A linear accelerator (Linac) capable of generating a series of X-ray beams;
2. A mechanism to position and orient the linear accelerator (and, hence, the X-ray beams);
3. A patient registration system to position and orient the target in the coordinate system of the delivery system;
4. A tracking system for tracking the target during treatment in case the target changes shape or moves between the time of, for example, an initial tracking X-ray of a pre-treatment computed tomography (CT) exam and the time of treatment, and/or during treatment due to respiration, patient-induced gross anatomical movement, and the like;
5. A couch capable of positioning the target (patient) independent of the mechanism described in #2 above.

In exemplary CyberKnife-based systems, the above 5 items may correspond to:

A 6 MeV X-band X-ray Linac
A 6 degree-of-freedom (DOF) robotic manipulator.
A patient registration system consisting of:
   Two ceiling-mounted diagnostic X-ray sources
   Two amorphous silicon image detectors mounted on the floor.
During treatment, two orthogonal X-rays are taken and registered with the CT data by cross-correlating the X-rays with simulated X-rays generated by CT data, called digitally reconstructed radiographs (DRR).
The tracking system may include several light-emitting diodes (LEDs) mounted on the patent's skin to provide additional information at a rate faster than what X-rays alone provide.
A couch with 5 DOF.

Figure 1:
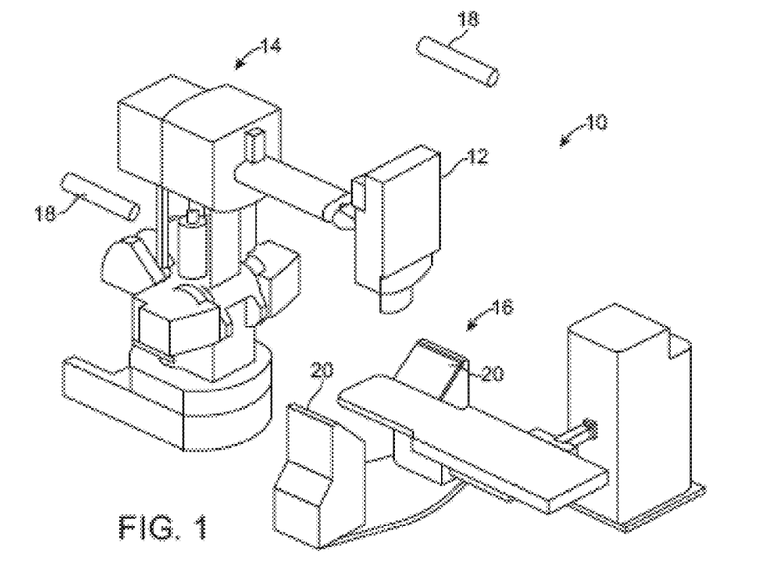
FIG. 1 is an exemplary CyberKnife stereotactic radiosurgery system for use in embodiments of the invention.

An exemplary CyberKnife stereotactic radiosurgery system 10 is illustrated in FIG. 1. Radiosurgery system 10 has a single source of radiation, which moves about relative to a patient. Radiosurgery system 10 includes a lightweight linear accelerator 12 mounted to a highly maneuverable robotic arm 14. An image guidance system 16 uses image registration techniques to determine the treatment site coordinates with respect to linear accelerator 12, and transmits the target coordinates to robot arm 14 which then directs a radiation beam to the treatment site. When the target moves, system 10 detects the change and corrects the beam. Hence, system 10 makes use of robot arm 14 and linear accelerator 12 under computer control. Image guidance system 16 includes diagnostic x-ray sources 18 and image detectors 20, this imaging hardware comprising two diagnostics fluoroscopes. These fluoroscopes provide a frame of reference for locating the patient's anatomy, which, in turn, has a known relationship to the reference frame of robot arm 14 and linear accelerator 12.

Typically, a target and its surrounding tissue are first imaged using CT, resulting in a volume of data. The target volume is then delineated in this CT volume and a desired dose to the target is prescribed. Delicate or other tissue structures of concern in the vicinity of the target are also delineated and may be assigned a maximum desired dose that can be deposited at these structures. A computer program then receives the location and the shape of the target and the critical structures, the prescribed doses and the geometric configuration of the radiation delivery system and computes (a) the position and orientation of the beams to be fired and (b) a contour diagram showing dose received by all voxels in the CT volume. The radiation oncologist then reviews this data to see if the target is receiving the right dose and if structures in the vicinity receive too much dose. He or she may modify the boundaries of the target and the critical structures, along with dose received by them, to reach an acceptable treatment plan.

During treatment delivery, the target can be first registered with the coordinate system of the treatment delivery system by using the patient registration system. The treatment delivery system may also receive the beam positions and orientations from the treatment planning stage. It then positions and orients the Linac and fires the beams towards the target.

A preferred robot manipulator may be capable of positioning and orienting the Linac so that it follows the target due to breathing. Since Fluoroscopic imaging may be disadvantageous for the entire duration of the radiation delivery (optionally about 2 hours or more) because it subjects the patient to extra radiation, the tracking system may first build an intra-operative correlation model between the motion of the skin of the patient recorded by the imaging of external light emitting diodes (LEDs) mounted to the skin of the patient and any fiducials implanted in the vicinity of the target and seen in the X-rays. (The tumor itself need not be visible in the X-rays). Tracking of the LEDs using one or more cameras oriented toward the skin of the patient can then be used to determine data regarding the respiration cycle and the positions of tissues that move with the respiration cycle. More specifically, intra-operative correlation models can be built by taking a series of X-ray images in quick succession for one or more breathing cycles and at the same time, recording the position of the skin using the signals from the LEDs. Following this, the LED signals alone may be used for at least a portion of the tracking X-rays may be intermittently acquired to verify the validity of the correlation model. If the model is no longer sufficiently valid, a fresh model is generated by following the same procedure as before.

Targets in the heart (tumors or other types of targets) pose two challenges for radiation delivery systems:

Implantation of fiducials in the heart muscle can be difficult and/or disadvantageous.
The heart itself beats fairly rapidly (for example, roughly at a rate of 1 beat every second), and some parts of the heart move more than the other parts due to this beating. In addition, the heart as a whole may also move due to respiration.

Figure 1A:
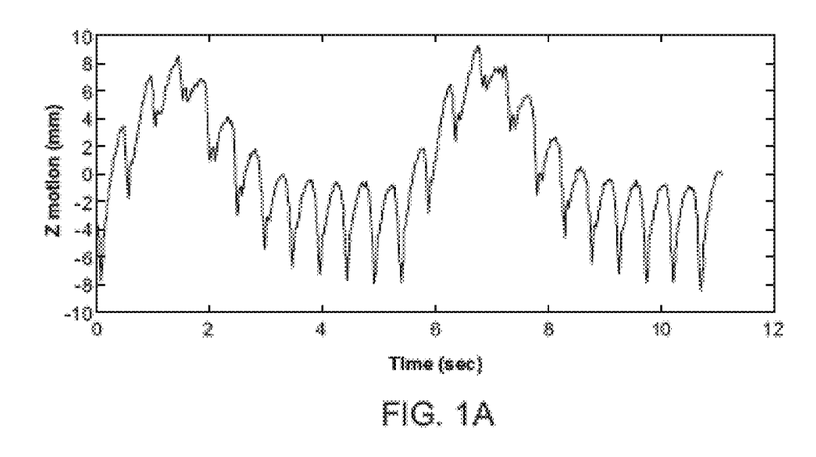
FIG. 1A is a graph showing exemplary data from the anterior/posterior motion of a point at the cavotricuspid isthmus inside the right atrium of a pig heart.

FIG. 1A graphically shows the anterior/posterior motion of a point at the cavotricuspid isthmus inside the right atrium of a pig heart. As can be seen, the motion has two components: a slow varying breathing component and a rapidly varying cardiac component.

Figure 2:
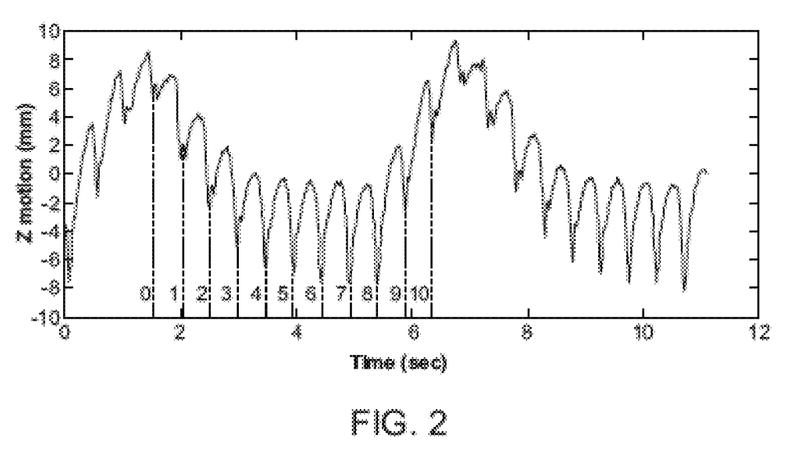
FIG. 2 is a graph similar to FIG. 1A showing timing for acquiring a time-sequence of 11 X-ray image pairs over 1 respiratory cycle at a common cardiac phase, $\Phi$.

Case 1: No (or Negligible) Cardiac Component; With Significant Respiratory Component In this case, the target in the heart muscle has only a respiratory component and not a cardiac component. Targets in the left atrium near the pulmonary veins may fall into this category. The steps may include:

1. Acquire a single CT volume at a cardiac phase, $\Phi$, of the cardiac cycle. Use a high speed CT scanner such as the 64-slice Siemens SOMOTOM Definition to acquire CT volumes quickly, e.g. one volume in 83 ms. Contrast agents may be used. Outline the target in this volume.
2. During patient registration stage, just prior to radiation delivery, acquire a series pairs of N X-rays, X-Rays(i), i=0, ..., N−1, and N samples of the signals from the LEDs, LEDs(i), over 1 respiratory cycle at the cardiac phase $\Phi$. FIG. 2 shows this scenario with N=11.
3. For each i=0, ..., N−1, register X-Rays(i) with the CT volume by correlating DRRs with X-rays(I) using a similarity measure or metric. The correlation focuses on registering structures of the heart visible in the DRRs and X-rays such as:
    Any natural landmarks of the heart such as points, lines, surfaces and volumes in, on, and/or around the heart. The silhouette of the heart is one such example. Other examples include parts of the esophagus, the trachea, the bronchial tree, the lungs, the ribs, the diaphragm, the clavicles, the right atrium, the left atrium, the right ventricle, the left ventricle, inferior vena cava, superior vena cava, ascending aorta, descending aorta, pulmonary veins, pulmonary arteries, the heart/lung border and the blood pool.
    Any artificial landmarks such as one or more fiducials inserted in to the esophagus, the trachea, the bronchial tree, or a catheter placed inside the heart.
4. Optionally, pre-process X-rays, CT volume or DRRs using techniques such as:
    Filtering (thresholding, gradient detection, curvature detection, edge enhancement, image enhancement, spatial frequency-based adaptive processing).
    Segmentation
    Mapping, such as windowing, nonlinear mapping
    Histogram equalization
    Spatial windowing, such as region-of-interest
    Higher order processing, such as connectivity model
    Temporal processing, such as filtering, convolving, differentiation, integration, motion analysis and optical flow.
5. Transform the target location from CT to the coordinate system of the treatment delivery system using the registration step in #3 above. Let the target location in the coordinate system of the treatment delivery system be P(i), i=0, ..., N−1.
6. Build a correlation model between the target and the LED signals using LEDs(i) as input and P(i), as output. Alternatively build a correlation model between the structures described in #3 above and the LED signals. The location of the target can be computed by adding the offset between the structures and the target to the motion of the structures predicted by the model.
7. Once the correlation model is built, use future samples of LEDs to position and orient the radiation beams.
8. Monitor the validity of the correlation model by acquiring X-ray images intermittently at the cardiac phase, $\Phi$, at any phase of the respiratory cycle.

In Step 2 above both X-ray images and LED signals can be acquired using either prospectively or retrospectively gating. In prospective gating, the ECG waveform may be analyzed by a system module and X-ray images and LED signals can be acquired when the cardiac phase $\Phi$ arrives in time. In retrospective gating, the X-ray images, LED signals and ECG samples are continuously acquired and saved with their respective time stamps. Later a separate module compares the time stamps of X-ray images and LED signals to the time stamps of the ECG samples to sort them into the appropriate cardiac phase. Alternatively, if retrospective gating is used, multiple CT volumes, CT(j), j=0, ..., M−1, at cardiac phases $\Phi(j)$ may be acquired in Step 1 and X-rays and LED signals in Step 2 may also be acquired at any one of the cardiac phases, $\Phi(j)$. The registration in Step 3 will then be done by using CT and X-ray images corresponding to the same cardiac phase, $\Phi(j)$.

Case 2: With Significant Cardiac Component and With Significant Respiratory Component The target in the heart muscle has both a respiratory component and a cardiac component. Targets in the ventricles near the valves fall into this category.

Figure 3:
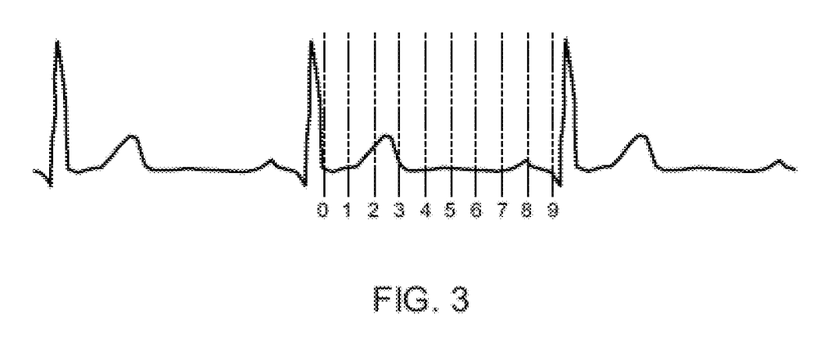
FIG. 3 is an illustration of an EKG waveform showing exemplary phases where a time-sequence of CT volumes are acquired.

Approach 1:
1. Acquire a series of M CT volumes, CT(j), j=0, ..., M−1, of the heart over one cardiac cycle with the patient holding his/her breath. Use a high speed CT scanner such as 64-slice Siemens SOMOTOM Definition to acquire CT volumes quickly, e.g. one volume in 83 ms. Contrast agents may be used.
2. FIG. 3 shows a typical EKG waveform with M=10 phases where 10 CT volumes are acquired. Outline the target in each of these M volumes. Alternatively, outline the target in one CT volume and automatically track it over all the CT volumes to generate the targets in other CT volumes.
3. Pick one of the CT phases, $\Phi$, as the reference phase. Acquire a series of pairs of N X-rays, X-rays(i), i=0, ..., N−1, and N samples of the signals from the LEDs, LED(i), over 1 respiratory cycle at the cardiac phase $\Phi$ as in Case 1 (FIG. 2) using prospective or retrospective cardiac gating as before. Build a correlation model between LEDs(i) and X-rays(i) by following steps 3, 4, 5 and 6 in Case 1 and using the CT data from the cardiac phase, $\Phi$.
4. Following this, use the LED signal, LEDs(i) signal to determine the location of the target in the CT volume corresponding to cardiac phase, $\Phi$, assuming the heart does not move due to cardiac motion (similar to Case 1). Then use the EKG signal, EKG(i), to determine the present cardiac phase, and add the offset off the target between the CT volumes of the present cardiac phase and the cardiac phase, $\Phi$, to superimpose the cardiac motion component, and thereby to determine the present target position.
5. Monitor the validity of the correlation model by acquiring X-ray images, X-rays(i), intermittently.

Figure 4:
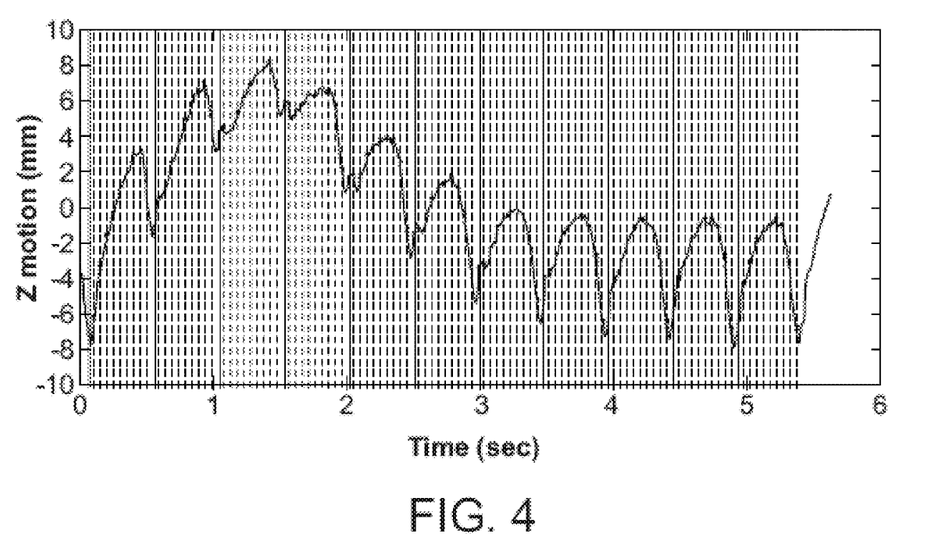
FIG. 4 is an illustration of M×N X-rays, LED signals and ECG signals as acquired over 1 respiratory cycle for use, for example, in an intra-operative motion prediction and validation model.

Approach 2:
1. Acquire a series of M CT volumes, CT(j), j=0, ..., M−1, of the heart over one cardiac cycle with the patient holding his/her breath. Use a high speed CT scanner such as 64-slice Siemens SOMOTOM Definition to acquire CT volumes quickly, e.g. one volume in 83 ms. Contrast agents may be used.
2. FIG. 3 shows a typical EKG waveform with M=10 phases where 10 CT volumes are acquired. Outline the target in each of these M volumes. Alternatively, outline the target in one CT volume and automatically track it over all the CT volumes to generate the targets in other CT volumes.
3. During patient registration stage, just prior to radiation delivery, over one respiratory cycle, acquire:
    A series pairs of N×M X-rays, X-rays(i, j),
    Using the LED signals, bin each X-ray image pair in to one of N respiratory phases and Using the ECG signals, bin each X-ray image pair in to one of M cardiac phases.

where, i=0, . . . , N−1, j=0, . . . , M−1, i iterates over the phases of a respiratory cycle and j iterates over the phases of a cardiac cycle. The respiratory cycle is divided in to N respiratory phases and each respiratory phase is divided in to M cardiac phases. FIG. 4 shows this scenario, schematically showing M cardiac phases during which a total of M×N X-rays. The X-ray acquisition can be prospectively or retrospectively to either or both respiratory and ECG cycles.

4. For each i=0, . . . , N−1 and j=0, . . . , M−1, register X-rays(i, j) with the CT(j) volume by correlating DRRs with X-rays(i, j). The correlation focuses on registering structures of the heart visible in the DRRs and X-rays such as:
   a. Any natural landmarks of the heart such as points, lines, surfaces and volumes in or on the heart. The silhouette of the heart is one such example, and other examples include those discussed above regarding Case 1.
   b. Any artificial landmarks such as one or more fiducials inserted in to the esophagus or a catheter placed inside the heart.
5. Optionally, pre-process X-rays, CT volume or DRRs using techniques such as:
   c. Filtering (thresholding, gradient detection, curvature detection, edge enhancement, image enhancement, spatial frequency-based adaptive processing).
   d. Segmentation
   e. Mapping, such as windowing, nonlinear mapping
   f. Histogram equalization
   g. Spatial windowing, such as region-of-interest
   h. Higher order processing, such as connectivity model
   i. Temporal processing, such as filtering, convolution, differentiation, integration, motion analysis and optical flow.
6. Transform the target location from CT(j) to each of the coordinate system of the treatment delivery system using the registration step in #4 above. Let the target location in the coordinate system of the treatment delivery system be P(i, j).
7. Build a correlation model between the target and the physiologic cycle data using the respiratory phase (such as the LED signal) and cardiac phase (such as EKG signal) as input and P(i, j) as the output. Alternatively build a correlation model between the structures described in #4 above and the respiratory and cardiac phases. The location of the target can be computed by adding the offset between the structures and the target to the motion of the structures predicted by the model.
8. Once the correlation model is built, monitor the respiratory and cardiac signals (using LED and EKG data) continuously, determine the respiratory and cardiac phases, predict the target location, P(I,j) and (j) to position and orient the radiation beams.
9. Monitor the validity of the correlation model by acquiring X-ray images, X-rays(i, j), and the corresponding respiratory and cardiac phases intermittently.

The present invention discloses a target motion simulator system that utilizes actuators to impart motion to the various components of the target motion simulator system, such as a radiation detection target, one or more fiducials, radiation-sensitive collateral tissue or critical structure, or other components. The actuators may simulate individual motion, such as respiratory or cardiac motion, or may simulate a combination of motions, such as both respiratory and cardiac motion. The actuators used for cardiac motion should be capable of motion similar to heart structures, for example speeds up to 5 cm/s and accelerations up to 20 cm/s$^2$. In order to achieve these speeds and accelerations, the radiation detector target mass must be minimized. Prior art test objects have used a structure or shell around the radiation detector in order to provide build up of absorbed dose in the tissue. Some of these prior art shells have been several centimeter thick and made of tissue equivalent materials. Shells of this sort are too massive to be accelerated easily and have been avoided in the present invention. Instead, dose modeling techniques are relied upon to provide accurate dose estimates without a shell for the radiation detector target. This is a conscious trade between dose measurement accuracy and motion fidelity that is justified by the significant effect that motion has on dose delivered to cardiac structures.

The actuators used in the target motion simulator system may be driven to simulate or match general physiologic position measurements or may simulate individual subjects. These measurements may be made using an electrophysiologic mapping system (CARTO) or biplane fluoroscopy. The CARTO mapping system records the position of a catheter inserted into the heart through a groin incision and was designed to determine a map of the atria of the heart for use for RF ablations. This system records 2 seconds of position data in order to determine an average location for a measurement point. By rapidly recording measurement points (less than 2 second intervals) while not changing catheter locations, the position of a single location can be recorded over 10-15 seconds.

Figure 5A:
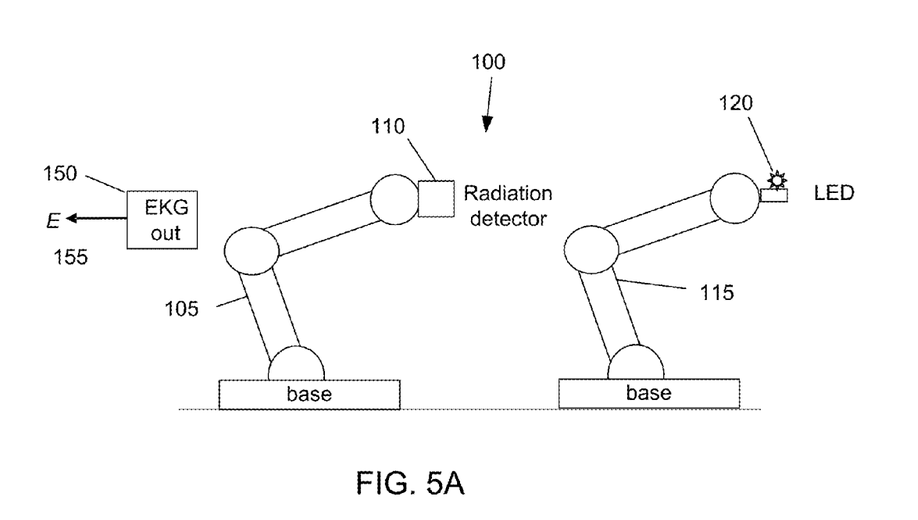
FIG. 5A shows one embodiment of the target motion simulator system including a first actuator moving a radiation detection target and a second actuator moving an external fiducial.

FIG. 5A shows one embodiment of the target motion simulator system 100 for use in verifying target tracking with a radiation therapy device, such as with the CyberKnife stereotactic radiosurgery system 10 in FIG. 1. The target motion simulator system 100 uses separate actuators for moving the components, including a first actuator 105 moving a radiation detection target 110 and a second actuator 115 moving an external fiducial 120. The radiation detection target 110 may include sensors and/or film to detect radiation hits and amounts, and may be a ball cube phantom. The actuators may be mounted on separate bases or a common base. The actuators can move with different, synchronized motions that are chosen to simulate the motions of structures in the heart due to respiratory and cardiac motion. For example, the first actuator 105 may simulate both a respiratory motion and a cardiac motion for the target 110. The second actuator 115 may simulate respiratory motion at another tissue site of the external fiducial 120, such as the chest surface. The motion of the second actuator 115 may be detected through the use of an LED 120 as the second fiducial. The respiratory motion and cardiac motion may be the same for each component, or they may be different, simulating movement of different locations within a body. The separate actuators are used to move the radiation detector targets and fiducial(s) so that differential motion can be imparted identical to the differential motion of the anatomic fiducial and target locations within a person. An EKG signal generator 150 is used to provide an EKG output signal E 155 that can be input to the radiation therapy device, such as the CyberKnife system.

Figure 5B:
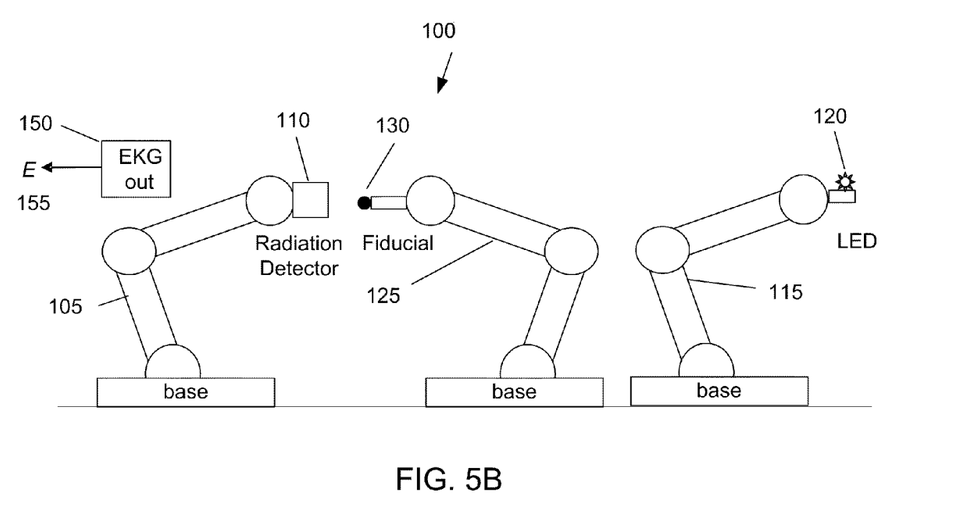
FIG. 5B shows another embodiment of the target motion simulator system of FIG. 5A further including a third actuator moving an internal fiducial.

FIG. 5B shows another embodiment of the target motion simulator system 100 of FIG. 5A having a third actuator 125 used to mimic the motion of an internal fiducial 130, for example, a portion of a catheter, radiation-sensitive collateral tissue or critical structure. The motion of the third actuator 125 may include respiratory motion, cardiac motion or both motions at the internal fiducial site.

Figure 6:
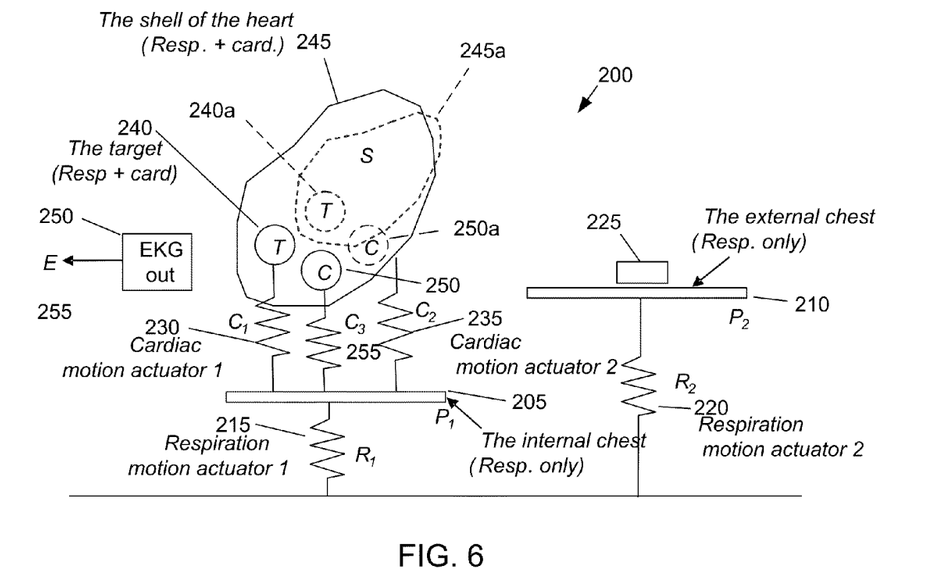
FIG. 6 shows another embodiment of the target motion simulator system.

FIG. 6 shows another embodiment of the target motion simulator system 200 having two platforms, P$_1$ 205 and P$_2$ 210. The platform P$_1$ 205, powered by the actuator R$_1$ 215, moves according to a respiratory motion internal to the chest, possibly at the heart. The platform P$_2$ 210, powered by the actuator $R_2$ 220, moves according to a respiratory motion at the chest (external) of the patient. An external fiducial 225, such as a synchrony tracking IR sensor, is mounted on $P_2$ 210. Mounted on the platform $P_1$ 205 are two cardiac actuators, $C_1$ 230 and $C_2$ 235, providing cardiac motion. The actuator $C_1$ 230 provides the cardiac motion at a radiation detection target T 240, while the actuator $C_2$ 235 provides cardiac motion of an internal fiducial, such as motion/deformation of a shell of the heart, S 245. An EKG signal generator 250 provides an EKG output signal E 255 that can be used by the CyberKnife system in tracking the target. Also shown is a radiation-sensitive collateral tissue or critical structure C 250 coupled to platform $P_1$ 205 with cardiac actuator $C_3$ 255 providing cardiac motion. Shown in broken line is target T 240a, fiducial S 245a, and critical structure C 250a at a different point in time.

The following are more detailed description of various components of the phantom:

1. The internal chest ($P_1$): This motion mimics the respiratory motion at the site of the heart, internal to the chest. Using the $R_1$, the user can program this motion.
   a. Degrees of freedom—initially perhaps 2 (anterior/posterior and superior/inferior translations)
   b. Min-Max, range of speeds and acceleration supported
2. The external chest ($P_2$): This motion mimics the respiratory motion at the outside of the chest, on the skin. Using the $R_2$, the user can program this motion. The Synchrony IR sensors will be mounted on this platform.
   a. Degrees of freedom—initially perhaps 2 (anterior/posterior and superior/inferior translations)
   b. Accuracy of phantom position during motion
3. The shell of the heart (S): The shell mimics the heart muscle/lung interface of the heart. In CT this interface should be visible and in X-rays and in DRRs, this interface should be visible as the cardiac silhouette. The silhouette will be used to track the motion during treatment. Ideally, the shell should move/deform periodically during the EKG cycle. The cardiac motion of S can be programmed using $C_2$, while the respiratory motion can be programmed using $R_1$.
   a. Degree of freedom: Initially the shape can be a blob that has no symmetry, that can oscillate back and forth around an axis.
   b. The shell includes any surrogate anatomical structures that can be tracked in X-rays, such as pulmonary veins, pulmonary arteries, trachea and bronchi, aorta, and any other structures in the heart.
4. The target (T): The target moves its own composite waveform containing both cardiac motion and the respiration. The cardiac motion of T can be programmed using $C_1$, while the respiratory motion can be programmed using $R_1$.
   a. Degrees of freedom: Initially perhaps 3 (anterior/posterior, superior/inferior and left/right translations)
   b. Ability to insert dosimetry film
   c. Spherical casing to avoid edge artifacts impacting tracking algorithms
5. EKG out: The phantom will generate a simulated EKG waveform synchronized with the cardiac motion that will serve as an input to the CyberHeart module.
6. Dosimetry film: The target should be able to hold a stack of dosimetry film in a manner similar to existing ball cube phantom targets used to evaluate CK dose delivery. Bang gel may also be used.
7. Radiation tolerance: The phantom should be able to withstand the scatter radiation from the CyberKnife beam (6 MeV). The target area should be able to withstand the radiation from the direct beam.
8. CT scan-ability: The phantom should be able to undergo 4D gated cardiac CT and not introduce artifacts affecting tracking algorithms.
9. X-ray imageability: The phantom should be able to undergo CyberKnife X-ray imaging and not introduce artifacts affecting tracking algorithms.
10. Size and weight: The phantom should be able to sit on the CyberKnife couch with the target positioned in the vicinity of room iso-center, as well has the couch of CT scanners. The smaller and the lighter the better.
11. Reliability: The phantom will be used by the customers. It should have undergone some product testing, although not to the same level as a clinical product.
12. Host: A PC should be able to interface with the phantom to control it.
13. Application Programming Interface: An application programming interface should be provided to control the phantom using the actuators, $R_1$, $R_2$, $C_1$ and $C_2$.
14. Cost: Reasonable
15. Power Supply: Should be consistent with countries where the phantom is used.

Note that all actuators can also carry any waveform, be it cardiac motion or respiratory motion or a combination of both. Motion can be provided using electric, pneumatic or hydraulic actuators. The shapes of the shell S 245, the target T 240 and critical structure C 250 can also be deforming over a physiologic cycle.

This test object is able to move faster in order to accurately follow the motion of the heart. In order to do this, the mass of the detector is reduced by removing shells that allow for absorbed dose build up.

Dose modeling is used to determine dose without the use of significant mass around the radiation detector.

This test object is able to move an object that will be used for tracking (the fiducial) and the radiation detector differently in order to determine the error introduced by tracking an object other than the ultimate target.

While other systems use water or tissue equivalent material surrounding the radiation detection target based on habitual demands for measurement accuracy, the present invention does not use this build up region. Using a radiation detector without this build up region reduces the accuracy of the radiation measurements, but motion of the heart demands this compromise and the modeling techniques disclosed herein are sufficiently accurate to allow the compromise to be made. In addition, the use of separate actuators to move the radiation detector and fiducial(s) separately is not obvious. The problem is not apparent for therapy targets outside of the heart region. Within the heart region, it is not obvious that separate actuators can be aligned and synchronized with the accuracy required.

The ability of a target motion simulator system to move a radiation detector target with the same motion as a cardiac structure was tested using an optical tracking system and CARTO position measurements of the cavotricuspid isthmus. In order to measure the position, an LED was attached to a ball-cube radiation detector that was attached to the motion actuator. The Accuray Synchrony system was used to track the position of the LED when the actuator moved the ball-cube with the motion of the cavotricuspid isthmus.

Figure 7:
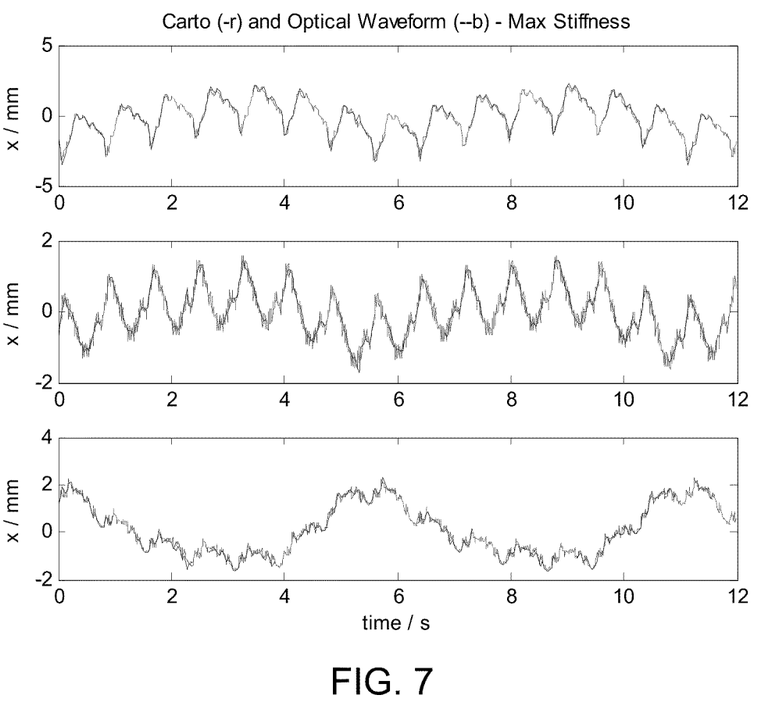
FIG. 7 shows the optical measurement of motion imparted to the radiation detector target by the actuator (blue) in comparison with a measured motion of a structure in the heart that was used as input (red).

FIG. 7 shows the optical measurement of motion imparted to the radiation detector target by the actuator (blue) in comparison with a measured motion of a structure in the heart that was used as input (red). The results show that the motion imparted to the radiation detector target (ball cube) accurately follows the driving waveform and is quite accurate for real motion of the heart. The position measurements also include high-frequency noise that is not tracked by the system.

Figure 8A:
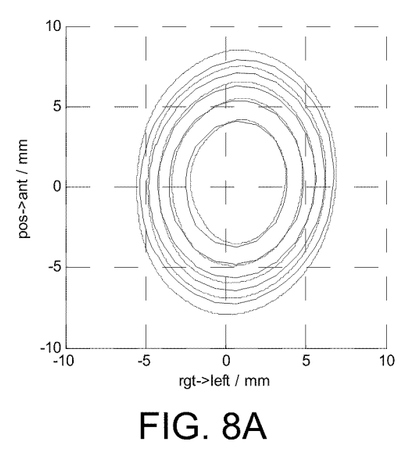
FIG. 8A shows the data collected for a stationary radiation detector.
Figure 8B:
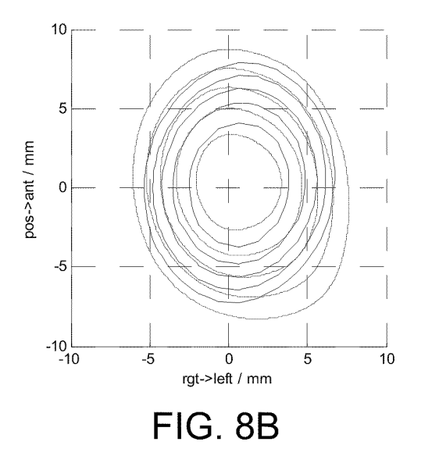
FIG. 8B shows the measurement when the radiation detector is moved to mimic the motion of the cavotricuspid isthmus.

FIGS. 8A and 8B show radiation measurements (red) compared to predictions from Accuray MuliPlan™. The graph in FIG. 8A shows the data collected for a stationary radiation detector. The graph in FIG. 8B shows the measurement when the radiation detector is moved to mimic the motion of the cavotricuspid isthmus. The prediction is much more accurate for the stationary detector than for the moving detector. This result supports compromising the detection accuracy in order to preserve motion accuracy.

Figure 9:
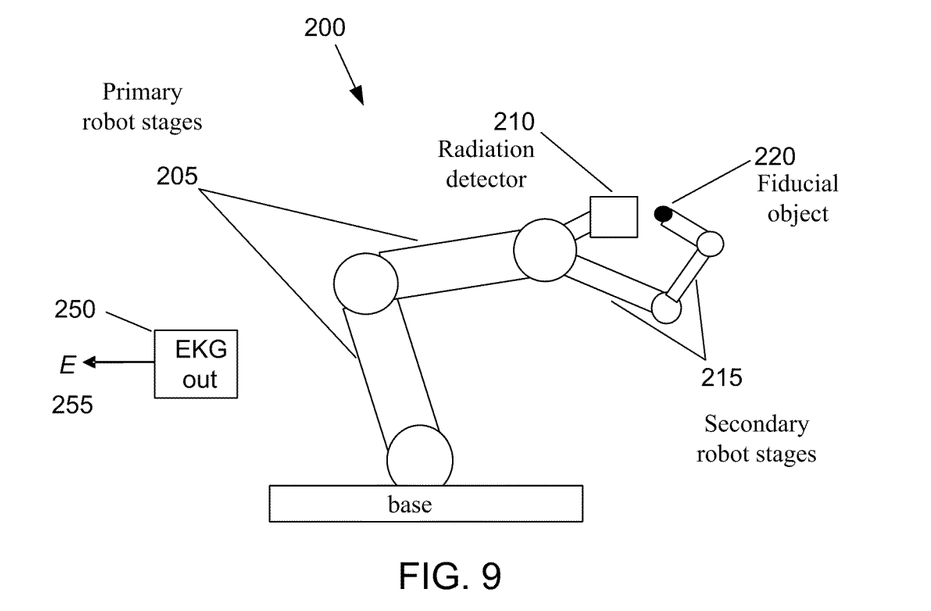
FIG. 9 shows another embodiment of the target motion simulator system.

A fiducial can be given different motion from the radiation detection target by attaching the fiducial and radiation detection target to different parts of a system that has redundant movement stages, such as shown in FIG. 9. Moving such a radiation detection target requires that the mass of the different stages be minimized in order to allow rapid motion.

FIG. 9 shows another embodiment of the target motion simulator system 200 for use in verifying target tracking with a radiation therapy device. The target motion simulator system 200 uses a primary actuator 205 moving a radiation detection target 210, a secondary actuators actuator 215 and an external fiducial 220. The secondary actuators actuator 215 moves the fiducial 220 with additional motion. The actuators can move with different, synchronized motions that are chosen to simulate the motions of structures in the heart due to respiratory and cardiac motion. For example, the primary actuator 205 may simulate both a respiratory motion and a cardiac motion for the target 210. The secondary actuator 215 may simulate respiratory and cardiac motion at another tissue site of the internal fiducial 220, such as the coronary sinus. The motion of the second actuator 215 may be detected through the use of an imaging system component of the treatment system detecting the fiducial 220. The respiratory motion and cardiac motion may be the same for each component, or they may be different, simulating movement of different locations within a body. The separate actuators are used to move the radiation detector targets and fiducial(s) so that differential motion can be imparted identical to the differential motion of the anatomic fiducial and target locations within a person. An EKG signal generator 250 is used to provide an EKG output signal E 255 that can be input to the radiation therapy device, such as the CyberKnife system. Additional secondary actuators (not shown) may be used to mimic the motion of an internal or external fiducial, for example, an external chest motion, radiation-sensitive collateral tissue or critical structure.

Figure 10:
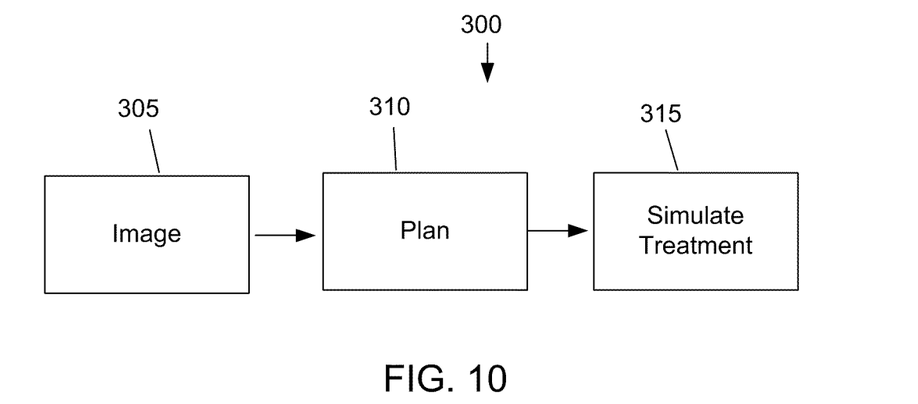
FIG. 10 shows the workflow of the simulated treatment process.

Referring now to FIG. 10, a relatively simple treatment flowchart 300 can represent steps used for simulating motion of a target having both respiratory and cardiac motion for use in verifying target tracking with a radiation therapy device, according to embodiments of the present invention. The radiation detection target and fiducials are imaged 305, typically using a remote imaging modality such as computed tomography (CT), magnetic resonance imaging (MRI), ultrasound imaging, X-ray imaging, optical coherence tomography, a combination of these or other imaging modalities, and/or the like. The imaging used in many embodiments may include a time sequence of three dimensional tissue volumes, with the time sequence typically spanning one or more cycles (such as a cardiac or heartbeat cycle, a respiration or breathing cycle, and/or the like).

Based on the images, a plan 310 will be prepared for simulating treatment of the radiation detection target, with the plan typically comprising a series of radiation beam trajectories which intersect within the radiation detection target. The radiation dose within the radiation detection target should be at least sufficient to provide the desired effect if it were actual target tissue. Embodiments of the invention may employ the 3-D volumes acquired in the imaging step 305 during the planning 310, with some embodiments making use of the motion model represented by the time sequence of 3-D tissue volumes so as to more accurately identify exposure of radiation outside of the radiation detection target, within radiation-sensitive collateral tissue models, inside the target, and the like. Planned timing of some or all of a series of radiation beams may be established based on the a synthetic physiological signal generator simulating a cardiac cycle, respiration cycle, and/or the like so as to generate the desired dosages within the radiation detection target, so as to minimize or inhibit radiation exposure to radiation-sensitive collateral tissue, and/or to provide desired gradients between the radiation detection target and radiation-sensitive collateral tissue. In some embodiments, the order of the planned radiation beams may be altered and/or the trajectories of the radiation beams may be calculated in response to the motion of the model volume.

Once the plan 310 is established, the simulated treatment 315 can be implemented. The simulated treatment will often make use of a processor to direct movement of a robotic structure supporting a radiation beam source, along with registration, validation, and/or tracking modules which enhance accuracy of the treatment. Tracking may employ the motion model developed during imaging 305, and/or may also employ a separate intra-operative motion model. The treatment 315 step and the associated hardware may use a sensor and/or input for physiological wave forms such as synthetic physiological signal generator synchronized with the radiation detection target and fiducials for use in such tracking.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A target motion simulator system for use in verifying target tracking with a radiation therapy device, the radiation therapy device configured to direct beams of radiation into a patient at a patient treatment location, the system comprising:
a radiation detection target coupled to a first motion actuator, the radiation detection target including a material sensative to the beams of radiation, the first motion actuator supporting the radiation detection target at the patient treatment location and configured to move the radiation detection relative to the radiation therapy device so as to simulate a first motion of a first tissue;
a fiducial coupled to a second motion actuator, the fiducial comprising an imageable structure and the first motion actuator supporting the fiducial and configured to move the fiducial relative to the radiation therapy device so as to simulate a second motion of a second tissue offset from the first tissue, a component of the first motion being asynchronous with the second motion; and
a synthetic electrocardiogram (EKG) signal generator synchronized with the component of the first motion, wherein an output signal from the generator is configured for transmission to the radiation therapy device so as to facilitate, in combination with a sensed position of the moving fiducial, the radiation therapy device in tracking the moving target while the radiation therapy device is direting the beams of radiation toward the moving target.

2. A target motion simulator system for use in verifying target tracking with a radiation therapy device, the radiation therapy device configured to direct beams of radiation at a moving tissue within a patient, the system comprising:
- a radiation detection target coupled to a first motion actuator, the radiation detection target including a material sensitive to the beams of radiation, the first motion actuator supporting the radiation detection target at a patient treatment location and configured to move the radiation detection target relative to the radiation therapy device so as to simulate both a first respiratory motion and a first cardiac motion of a first tissue;
- a fiducial coupled to a second motion actuator, the fiducial comprising an imageable structure and the first motion actuator supporting the fiducial and configured to move the fiducial relative to the radiation therapy device so as to simulate a second respiratory motion of a second tissue offset from the first tissue; and
- an electrocardiogram (EKG) output signal generator synchronized with the first cardiac motion, wherein an EKG output signal from the EKG signal generator, in combination with a sensed fiducial position signal, facilitates tracking of the moving target by the radiation therapy device.

3. The system of claim 2, further comprising an internal fiducial coupled to a third motion actuator simulating both the first respiratory motion and a second cardiac motion.

4. The system of claim 3, wherein the first and second cardiac motions correspond in orientation, phase, and magnitude.

5. The system of claim 3, wherein the first and second cardiac motions comprise differing orientations, phases, and/or magnitudes.

6. The system of claim 3, further comprising a radiation-sensitive collateral tissue structure model coupled to a fourth motion actuator simulating both the first respiratory motion and a third cardiac motion.

7. The system of claim 6, wherein the radiation-sensitive structure model includes a radiation detector.

8. The system of claim 2, wherein the internal fiducial comprises a deformable heart shell around the target or proximate the target.

9. The system of claim 2, wherein the internal fiducial comprises a portion of a catheter.

10. The system of claim 2, wherein the radiation detection target includes a dosimetry film holder.

11. The system of claim 2, further comprising a control system coupled to the respiratory and cardiac motion actuators and the EKG signal generator.

12. The system of claim 2, wherein the first respiratory motion simulates internal chest respiratory motion within a chest cavity.

13. The system of claim 2, wherein the first cardiac motion simulates cardiac motion within a chest cavity.

14. The system of claim 2, wherein the second respiratory motion simulates external chest motion on a chest surface.

15. The system of claim 2, wherein the external fiducial comprises a tracking sensor.

16. A target motion simulator system for simulating motion of a target having both respiratory and cardiac motion for use in verifying target tracking with a radiation therapy device, the radiation therapy device configured to direct beams of radiation into a patient at a patient treatment location, the system comprising:
- an internal chest simulator coupled to a first respiratory motion actuator, the first respiratory motion actuator configured to move so as to simulate internal chest respiratory motion;
- a radiation detection target movably supported by the internal chest simulator so that movement of the internal chest simutor moves the radiation detection target with a first cardiac motion actuator simulating a first cardiac motion, wherein the target movement includes both internal chest respiratory motion and first cardiac motion;
- an external skin simulator coupled to a second respiratory motion actuator, the second respiratory motion actuator supporting the external skin simulator and configured to move the external skin simulator relative to the radiation therapy device so as to simulate external skin respiratory motion;
- an external fiducial coupled to the external skin simulator; and
- an electrocardiogram (EKG) output signal generator synchronized with the first cardiac motion, wherein an EKG output signal from the EKG signal generator may be used by the radiation therapy device in tracking the target.

17. A method of using a target motion simulator system having both respiratory and cardiac motion for use in verifying target tracking with a radiation therapy device, the method comprising:
- moving, with a first motion actuator, a radiation detection target with both a first respiratory motion and a first cardiac motion;
- moving, with a second motion actuator, a fiducial with a second respiratory motion;
- simulating an electrocardiogram (EKG) output signal synchronized with the first cardiac motion;
- tracking the radiation detection target with the radiation therapy device using input from the EKG output signal and the external fiducial movement; and
- firing a radiation dose from the radiation therapy device at the target.

18. The method of claim 17, further comprising determining radiation received by the target.

19. The method of claim 17, further comprising:
- moving an internal fiducial with the first respiratory motion and a second cardiac motion; and
- tracking the internal fiducial with the radiation therapy device, wherein the radiation therapy device uses input from the internal fiducial movement in tracking the radiation detection target.

20. The method of claim 17, further comprising:
- moving a model of a radiation-sensitive collateral tissue structure with both the first respiratory motion and a third cardiac motion; and
- determining radiation received by the radiation-sensitive collateral tissue structure.

21. A method of using a target motion simulator system having both respiratory and cardiac motion for use in verifying target tracking with a radiation therapy device, the method comprising:
- moving, with a first motion actuator, an internal chest simulator simulating an internal chest respiratory motion;
- moving, with a second motion actuator, a radiation detection target coupled to the internal chest simulator simulating a first cardiac motion;

moving, with a third motion actuator, an external fiducial coupled to an external skin simulator simulating external skin respiratory motion;

simulating an electrocardiogram (EKG) output signal synchronized with the first cardiac motion;

tracking the radiation detection target and external fiducial with the radiation therapy device using input from the EKG output signal and the external fiducial movement; and firing a radiation from the radiation therapy device at the target.

22. The method of claim 21, further comprising determining radiation received by the target.

23. The method of claim 21, further comprising:

moving an internal fiducial coupled to the internal chest simulator simulating a second cardiac motion; and tracking the internal fiducial with the radiation therapy device, wherein the radiation therapy device uses input from the internal fiducial movement in tracking the radiation detection target.

24. The method of claim 21, further comprising:

moving a radiation-sensitive collateral tissue structure coupled to the internal chest simulator simulating a third cardiac motion; and determining radiation received by the radiation-sensitive collateral tissue structure.

25. A simulator system for simulating motion of a target for use in verifying target tracking with a radiation therapy device comprising:

a movable primary actuator stage;

a radiation detection target coupled to the primary actuator stage with a first movable secondary actuator stage, a combination of movement from the primary actuator stage and first secondary actuator stage simulating both a first respiratory motion and a first cardiac motion;

a fiducial coupled to the primary actuator stage with a second movable secondary actuator stage, a combination of movement from the primary actuator stage and second secondary actuator stage simulating a second respiratory motion; and an electrocardiogram (EKG) output signal synchronized with the first cardiac motion, wherein the EKG output signal may be used by the radiation therapy device in tracking the target.

26. The system of claim 25, wherein the radiation detection target includes a dosimetry film holder.

27. The system of claim 25, wherein the first respiratory motion simulates internal chest respiratory motion within a chest cavity.

28. The system of claim 25, wherein the first cardiac motion simulates cardiac motion within a chest cavity.

29. The system of claim 25, wherein the second respiratory motion simulates external chest motion on a chest surface.

30. The system of claim 25, wherein the secondary robot stage further simulates a second cardiac motion.

* * * * *